United States Patent
Kleiner et al.

(10) Patent No.: US 8,685,433 B2
(45) Date of Patent: Apr. 1, 2014

(54) ABSORBABLE COATING FOR IMPLANTABLE DEVICE

(75) Inventors: Lothar W. Kleiner, Los Altos, CA (US); Syed F. A. Hossainy, Hayward, CA (US); Mikael Trollsas, San Jose, CA (US); Stephen D. Pacetti, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 241 days.

(21) Appl. No.: 12/751,989

(22) Filed: Mar. 31, 2010

(65) Prior Publication Data

US 2011/0244017 A1 Oct. 6, 2011

(51) Int. Cl.
- *A61L 31/10* (2006.01)
- *A61L 31/16* (2006.01)
- *C08L 67/04* (2006.01)

(52) U.S. Cl.
USPC .......... 424/426; 424/94.4; 427/2.1; 427/2.25; 514/180; 514/181; 514/182; 514/21.3; 514/211.08; 514/252.18; 514/291; 514/449; 514/545

(58) Field of Classification Search
None
See application file for complete search history.

(56) References Cited

U.S. PATENT DOCUMENTS

| 2004/0009226 A1* | 1/2004 | McHugh et al. ............. 424/486 |
| 2004/0106987 A1* | 6/2004 | Palasis et al. ............... 623/1.42 |
| 2007/0078513 A1 | 4/2007 | Campbell |
| 2009/0216316 A1* | 8/2009 | Wang .......................... 623/1.38 |

FOREIGN PATENT DOCUMENTS

| WO | WO 2004/026361 | 4/2004 |
| WO | WO 2007/062036 | 5/2007 |
| WO | WO 2009/108490 | 9/2009 |

OTHER PUBLICATIONS

International Search Report for PCT/US2011/026794, mailed May 30, 2011, 4 pgs.
Harper, "Drug Lantentation", Prog. Drug. Res. 4, pp. 221-294 (1962).
Martin et al., "Enhancing the biological activity of immobilized osteopontin using a type-1 collagen affinity coating", Wiley Periodicals, Inc. pp. 10-19 (2004).
Sinkula et al., "Rationale for design of biologically reversible drug derivatives: Prodrugs", J. of Pharmaceutical Sciences vol. 64, No. 2 (1975).
Spagnuolo et al., "Gas1 is induced by VE—cadherin and vascular endothelial growth factor and inhibits endothelial cell apoptosis", Blood, vol. 103, No. 8, pp. 3005-3012 (2004).
Stella et al., "Prodrugs Do They Have Advantages in Clinical Practice?", Drugs 29, pp. 455-473 (1985).
Völkel et al., "Targeting of immunoliposomes to endothelial cells using a single-chain Fv fragment directed against human endoglin (CD105)", Biochimica et Biophysica Acta 1663 pp. 158-166 (2004).

* cited by examiner

*Primary Examiner* — Suzanne Ziska
(74) *Attorney, Agent, or Firm* — Squire Sanders (US) LLP

(57) ABSTRACT

The present invention provides an absorbable coating for an implantable device and the methods of making and using the same.

18 Claims, No Drawings

ABSORBABLE COATING FOR IMPLANTABLE DEVICE

FIELD OF THE INVENTION

The present invention relates to an absorbable coating an implantable device and methods of making and using the same.

BACKGROUND OF THE INVENTION

Percutaneous coronary intervention (PCI) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress the atherosclerotic plaque of the lesion to remodel the lumen wall. The balloon is then deflated to a smaller profile to allow the catheter to be withdrawn from the patient's vasculature.

Problems associated with the above procedure include formation of intimal flaps or torn arterial linings which can collapse and occlude the blood conduit after the balloon is deflated. Moreover, thrombosis and restenosis of the artery may develop over several months after the procedure, which may require another angioplasty procedure or a surgical bypass operation. To reduce the partial or total occlusion of the artery by the collapse of the arterial lining and to reduce the chance of thrombosis or restenosis, a stent is implanted in the artery to keep the artery open.

Drug eluting stents have reduced the incidence of in-stent restenosis (ISR) after PCI (see, e.g., Serruys, P. W., et al., J. Am. Coll. Cardiol. 39:393-399 (2002)), which has plagued interventional cardiology for more than a decade. However, a few challenges remain in the art of drug eluting stents. For example, compromised coating integrity when an amorphous bioabsorbable polymer is used for coating a stent, which can result from the conditions of ethylene oxide (ETO) sterilization or from the conditions of crimping a stent onto the delivery balloon. Conditions such as elevated temperature, high relative humidity, and high concentration of ETO in the ETO sterilization process can result in plasticization and adhesion of the coating to the balloon via polymer deformation and flow. In a similar way, a completely amorphous bioabsorbable polymer may flow when crimped at temperatures above the polymer glass transition temperature ($T_g$) on to the delivery balloon.

Aliphatic polyesters are used in pharmaceutical and biomedical applications, including for example surgical sutures and drug delivery systems. Poly(L-lactide) (PLLA) is one of the most widely studied polymer biomaterials, attractive for its biodegradable and biocompatible properties. However, PLLA is not ideally suited for many aspects of drug delivery systems, including those involving drug-eluting stents. Issues of L-lactide based drug delivery stent systems include compromised mechanical properties after the fabrication process and deployment of such systems, and a sometimes relatively long absorption period.

The embodiments of the present invention address the above-identified needs and issues.

SUMMARY OF THE INVENTION

In one aspect, the present invention provides a bioabsorbable coating on an implantable medical device. The coating comprises a primer layer comprising a bioabsorbable polymer having a first molecular weight and a second layer comprising a bioabsorbable polymer of a second molecular weight. The first molecular weight is higher than the second molecular weight, and the coating is completely or substantially completely absorbed upon implantation in a human body within a period from about 3 months to about 6 months.

In some embodiments, the primer layer comprises a high or very high molecular weight (HMW or VHMW) absorbable polymer. Examples of such HMW or VHMW absorbable polymer are PLLA, 85/15 PLGA, 75/25 PLGA, poly(ester amide), PLA-PCL-GA terpolymer, PCL-GA, and copolymers thereof.

In some embodiments, optionally in combination with the various embodiments above, the second layer comprises a low molecular weight (LMW) absorbable polymer. An example of the LMW absorbable polymer is LMW D,L-PLA.

In some embodiments, optionally in combination with the various embodiments above, the second layer comprises a drug or a drug embedded in an absorbable polymer.

In some embodiments, optionally in combination with the various embodiments above, the second layer does not comprise a drug and is formed on top of a layer of a drug on top of the primer layer.

In some embodiments, optionally in combination with the various embodiments above, the coating disclosed herein is micro-porous and is formed by a process of controlled phase inversion kinetics, wherein the second layer and/or the primer layer can include D,L-PLA.

In some embodiments, optionally in combination with the various embodiments above, the implantable device is a stent.

In some embodiments, optionally in combination with the various embodiments above, the second layer comprises a drug selected from the group consisting of are paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (ABT-578), zotarolimus, novolimus, myolimus, temsirolimus, deforolimus, γ-hiridun, clobetasol, pimecrolimus, imatinib mesylate, midostaurin, feno fibrate, prodrugs thereof, co-drugs thereof, and combinations thereof.

In another aspect, the present invention provides a method of fabricating an implantable device. The method comprises:
  forming a primer layer on surface of an implantable device comprising a high molecular weight (HMW) or very high molecular weight (VHMW) absorbable polymer; and
  forming a second layer comprising a low molecular weight (LMW) absorbable polymer, thereby forming the coating, wherein the first molecular weight is higher than the second molecular weight,
  wherein the coating is completely or substantially completely absorbed upon implantation in a human body within a period from about 3 months to about 6 months.

In some embodiments, the primer layer comprises a high or very high molecular weight (HMW or VHMW) absorbable polymer. Examples of such HMW or VHMW absorbable polymer are PLLA, 85/15 PLGA, 75/25 PLGA, poly(ester amide), PLA-PCL-GA terpolymer, PCL-GA, and copolymers thereof.

In some embodiments, optionally in combination with the various embodiments above, the second layer comprises a low molecular weight (LMW) absorbable polymer. An example of the LMW absorbable polymer is LMW D,L-PLA.

In some embodiments, optionally in combination with the various embodiments above, the second layer comprises a drug.

In some embodiments, optionally in combination with the various embodiments above, the second layer does not comprise a drug and is formed on top of a layer of a drug on top of the primer layer.

In some embodiments, optionally in combination with the various embodiments above, the coating disclosed herein is micro-porous and is formed by a process of controlled phase inversion kinetics, wherein the second layer and/or the primer layer can include D,L-PLA.

In some embodiments, optionally in combination with the various embodiments above, the implantable device is a stent.

In some embodiments, optionally in combination with the various embodiments above, the second layer comprises a drug selected from the group consisting of are paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), zotarolimus, novolimus, myolimus, temsirolimus, deforolimus, γ-hiridun, clobetasol, pimecrolimus, imatinib mesylate, midostaurin, feno fibrate, prodrugs thereof, co-drugs thereof, and combinations thereof.

In some embodiments, optionally in combination with the various embodiments above, the method further comprises enhancing the degradation rate of the coating, which enhancing degradation rate can be, for example, decreasing the molecular weight of the bioabsorbable polymer in the first and/or second post coating prior to deployment of the implantable device, or enhancing the rate of hydrolysis of the bioabsorbable polymer in the first and/or second layer.

In some embodiments, optionally in combination with the various embodiments above, enhancing the degradation rate of the coating comprises a step selected from:

i) prolonged e-beaming, multiple e-beaming post coating, e-beaming at a lower dose rate for a total longer time under the beam, or e-beaming at room temperature;
ii) higher temperature treatment of a coated implantable device for longer time drying in a high humidity environment prior to vacuum/conventional drying;
iii) decreasing the BHT content in the coating if the coating comprises BHT;
iv) adding lactide monomers and/or oligomers in the coating;
v) adding —COOH terminated oligomers of D,L-PLA in the coating;
vi) sterilization by gamma radiation at the same dose (i.e. 31 kGy) as would be used for e-beam;
vii) adding in the coating a plasticizer selected from ethyl lactate, DMSO, NMP, and benzyl benzoate so as to lower the glass transition temperature ($T_g$) of the coating to accelerate degradation;
viii) adding a hygroscopic additive in a coating;
ix) adding micronized $NaO_2$ or $KO_2$, or superoxide salts in the coating;
x) adding more stannous octoate to bring its level up to the maximum level allowed by the material specification.
xi) adding LMW D,L-PLA with a MW tuned to degrade within 3 to 6 months;
xii) forming micro-porous D,L-PLA coating by a process of controlled phase inversion kinetics; and
xiii) any combination of step i)-xii).

In a still further aspect of the present invention, it is provided a method of treating, preventing, or ameliorating a vascular medical condition, comprising implanting in a patient an implantable medical comprising any of the implantable article described above. The vascular medical condition can be restenosis, atherosclerosis, thrombosis, hemorrhage, vascular dissection or perforation, vascular aneurysm, vulnerable plaque, chronic total occlusion, claudication, anastomotic proliferation (for vein and artificial grafts), bile duct obstruction, ureter obstruction, tumor obstruction, or combinations of these.

DETAILED DESCRIPTION

In one aspect, the present invention provides a bioabsorbable coating on an implantable medical device. The coating has an absorption period from about three months to about six months during which the coating is completely or substantially completely absorbed upon implantation in a human body. The coating comprises a primer layer on surface of the implantable device comprising a bioabsorbable polymer having a first molecular weight and a second layer comprising a bioabsorbable polymer of a second molecular weight, where the first molecular weight is higher than the second molecular weight. In some embodiments, the coating comprises a primer layer comprising a high or very high molecular weight (HMW or VHMW) absorbable polymer; and a second layer comprising a low molecular weight (LMW) absorbable polymer. The second layer can be a topcoat on top of a layer of a drug or a matrix layer where the matrix layer may or may not include a drug. In some embodiments, the matrix layer can include a drug.

In a second aspect, the present invention provides a method of fabricating an implantable device. The method comprises providing an implantable device and forming a coating on the implantable device. The coating has an absorption period from about three months to about six months during which the coating is completely or substantially completely absorbed upon implantation in a human body. The coating comprises a primer layer on surface of the implantable device comprising a bioabsorbable polymer having a first molecular weight and a second layer comprising a bioabsorbable polymer of a second molecular weight, where the first molecular weight is higher than the second molecular weight. In some embodiments, forming a coating comprises: a) forming a primer layer on surface of the implantable device comprising a HMW or VHMW absorbable polymer; b) forming a second layer comprising a LMW absorbable polymer, thereby forming the coating. The second layer can be a topcoat on top of a layer of a drug or a matrix layer where the matrix layer may or may not include a drug. In some embodiments, the matrix layer can include a drug.

Suitable HMW absorbable polymer as primer generally has high elongation. Examples of such HMW absorbable polymers include, e.g., VHMW PLLA, 85/15 PLGA, HMW or VHMW 75/25 PLGA, HMW or VHMW poly(ester amide) (elastomeric), HMW or VHMW PLA-PCL-GA terpolymer, HMW or VHMW PCL-GA, or copolymers thereof.

Additional examples include poly(β-hydroxybutyrate) (PHB), copolymers of 3-hydroxybutyrate (3HB) and 3-hydroxyvalerate (3HV), random copolymers of 3HB and 4HV, polycarbonates, polyanhydrides, poly(phosphate esters), polyphosphazenes, and poly(orthoesters).

As used herein, the term HMW refers to a molecular weight about 60,000 Daltons and below about 200,000 Daltons. The term VHMW refers to a molecular weight about 200,000 Daltons or above. Conversely, the term LMW refers to a number average molecular weight below 60,000 Daltons, e.g., 57,000 Daltons.

In some embodiments, optionally in combination with any one or combinations of the above embodiments, the method further comprises increasing the rate of absorption of the coating described above by decreasing the molecular weight of the polymer in the coating. Decreasing the molecular weight of the polymer in the coating can be achieved by various established methods. Such methods, which are described in detail below, include, for example, a prolonged e-beam process post coating to decrease the molecular weight of the polymer in the coating. In some embodiments, such method includes, e.g., selecting a commercial polymer of a desired molecular weight or a commercial absorbable polymer having an acid end group, and forming the second layer using commercial polymer.

In some embodiments, optionally with one or any combination of features of the various embodiments above, the stent or the coating further comprises a bioactive agent. Examples of the bioactive agent are paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), zotarolimus, myolimus, novolimus, temsirolimus, deforolimus, γ-hiridun, clobetasol, pimecrolimus, imatinib mesylate, midostaurin, feno fibrate, prodrugs thereof, co-drugs thereof, and combinations thereof.

The implantable article described herein is generally degradable or bioabsorbable. In some embodiments, the coating can degrade within about 1 month, 2 months, 3 months, 4 months, or 6 months after implantation of an implantable device comprising the coating.

In some embodiments, the implantable article (e.g., an implantable medical device or a coating on an implantable medical device such as stent) can include one or more other biocompatible polymers, which are described below.

The implantable device described herein, such as a stent, can be implanted in a patient to treat, prevent, mitigate, or reduce a vascular medical condition, or to provide a pro-healing effect. In some embodiments, the vascular medical condition or vascular condition is a coronary artery disease (CAD) and/or a peripheral vascular disease (PVD). Some examples of such vascular medical diseases are restenosis and/or atherosclerosis. Some other examples of these conditions include thrombosis, hemorrhage, vascular dissection or perforation, vascular aneurysm, vulnerable plaque, chronic total occlusion, claudication, anastomotic proliferation (for vein and artificial grafts), bile duct obstruction, ureter obstruction, tumor obstruction, or combinations of these.

DEFINITIONS

Wherever applicable, the definitions to some terms used throughout the description of the present invention as provided below shall apply.

The terms "biologically degradable" (or "biodegradable"), "biologically erodable" (or "bioerodable"), "biologically absorbable" (or "bioabsorbable"), and "biologically resorbable" (or "bioresorbable"), in reference to polymers and coatings, are sometimes used interchangeably and refer to polymers and coatings that are capable of being completely or substantially completely degraded, dissolved, and/or eroded over time when exposed to physiological conditions and can be gradually resorbed, absorbed and/or eliminated by the body, or that can be degraded into fragments that can pass through the kidney membrane of an animal (e.g., a human), e.g., fragments having a molecular weight of about 40,000 Daltons (40 kDa) or less. The process of breaking down and eventual absorption and elimination of the polymer or coating can be caused by, e.g., hydrolysis, metabolic processes, oxidation, enzymatic processes, bulk or surface erosion, and the like. In some embodiments, a distinction can be made between bioresorbable and bioabsorbable where a bioresorbable polymer refers to one whose degradants the body can use whereas a bioabsorbable polymer refers to one whose degradants the body eliminates. Conversely, a "biostable" polymer or coating refers to a polymer or coating that is not biodegradable.

Whenever the reference is made to "biologically degradable," "biologically erodable," "biologically absorbable," and "biologically resorbable" stent coatings or polymers forming such stent coatings, it is understood that after the process of degradation, erosion, absorption, and/or resorption has been completed or substantially completed, no coating or substantially little coating will remain on the stent. Whenever the terms "degradable," "biodegradable," or "biologically degradable" are used in this application, they are intended to broadly include biologically degradable, biologically erodable, biologically absorbable, and biologically resorbable polymers or coatings.

As used herein, the term "complete degradation" or "completely degrade" shall be the state of full degradation or absorption of the coating. The term "substantially complete degradation" or "substantially completely degrade" shall mean a state of degradation where at least 80% of the coating is degraded, absorbed, or eroded. In some embodiments, "substantially complete degradation" or "substantially completely degrade" shall mean about 80% to about 99%, about 85% to about 99%, about 90% to about 99%, or about 95% to about 99% by weight of a coating is degraded, absorbed, or eroded.

"Physiological conditions" refer to conditions to which an implant is exposed within the body of an animal (e.g., a human). Physiological conditions include, but are not limited to, "normal" body temperature for that species of animal (approximately 37° C. for a human) and an aqueous environment of physiologic ionic strength, pH and enzymes. In some cases, the body temperature of a particular animal may be above or below what would be considered "normal" body temperature for that species of animal. For example, the body temperature of a human may be above or below approximately 37° C. in certain cases. The scope of the present invention encompasses such cases where the physiological conditions (e.g., body temperature) of an animal are not considered "normal."

As used herein, the term "micro-porous" refers to a coating micro-scale pores, depots, channels, or cavity. The coating can have a porosity from about 5% to about 50%, from about 5% to about 40%, from about 5% to about 40%, from about 5% to about 40%, from about 10% to about 50%, from about 10% to about 40%, from about 10% to about 30%, from about 10% to about 20%, from about 20% to about 50%, from about 20% to about 40%, from about 20% to about 30%, from about 30% to about 50%, from about 30% to about 40%, or from about 40% to about 50% by volume. Specific examples of porosity in such a coating can be about 10%, about 20%, about 30, about 40, or about 50% by volume. The higher the porosity, the higher the rate of water uptake and the higher the equilibrium water content. This results in an enhanced rate of hydrolysis of the coating.

In the context of a blood-contacting implantable device, a "prohealing" drug or agent refers to a drug or agent that has the property that it promotes or enhances re-endothelialization kinetics of arterial lumen to promote healing of the vascular tissue.

As used herein, a "co-drug" is a drug that is administered concurrently or sequentially with another drug to achieve a particular pharmacological effect. The effect may be general or specific. The co-drug may exert an effect different from that of the other drug, or it may promote, enhance or potentiate the effect of the other drug.

As used herein, the term "prodrug" refers to an agent rendered less active by a chemical or biological moiety, which metabolizes into or undergoes in vivo hydrolysis to form a drug or an active ingredient thereof. The term "prodrug" can be used interchangeably with terms such as "proagent", "latentiated drugs", "bioreversible derivatives", and "congeners". N. J. Harper, Drug latentiation, *Prog Drug Res.*, 4: 221-294 (1962); E. B. Roche, Design of Biopharmaceutical Properties through Prodrugs and Analogs, Washington, D.C.: American Pharmaceutical Association (1977); A. A. Sinkula and S. H. Yalkowsky, Rationale for design of biologically reversible drug derivatives: prodrugs, *J. Pharm. Sci.*, 64: 181-210 (1975). Use of the term "prodrug" usually implies a covalent link between a drug and a chemical moiety, though some authors also use it to characterize some forms of salts of the active drug molecule. Although there is no strict universal definition of a prodrug itself, and the definition may vary from author to author, prodrugs can generally be defined as pharmacologically less active chemical derivatives that can be converted in vivo, enzymatically or nonenzymatically, to the active, or more active, drug molecules that exert a therapeutic, prophylactic or diagnostic effect. Sinkula and Yalkowsky, above; V. J. Stella et al., Prodrugs: Do they have advantages in clinical practice?, *Drugs*, 29: 455-473 (1985).

The terms "polymer" and "polymeric" refer to compounds that are the product of a polymerization reaction. These terms are inclusive of homopolymers (i.e., polymers obtained by polymerizing one type of monomer), copolymers (i.e., polymers obtained by polymerizing two or more different types of monomers), terpolymers, etc., including random, alternating, block, graft, dendritic, crosslinked and any other variations thereof.

As used herein, the term "implantable" refers to the attribute of being implantable in a mammal (e.g., a human being or patient) that meets the mechanical, physical, chemical, biological, and pharmacological requirements of a device provided by laws and regulations of a governmental agency (e.g., the U.S. FDA) such that the device is safe and effective for use as indicated by the device. As used herein, an "implantable device" may be any suitable substrate that can be implanted in a human or non-human animal. Examples of implantable devices include, but are not limited to, self-expandable stents, balloon-expandable stents, coronary stents, peripheral stents, stent-grafts, shunts, catheters, other expandable tubular devices for various bodily lumen or orifices, grafts, vascular grafts, arteriovenous grafts, by-pass grafts, pacemakers and defibrillators, leads and electrodes for the preceding, artificial heart valves, anastomotic clips, arterial closure devices, patent foramen ovale closure devices, cerebrospinal fluid shunts, and particles (e.g., drug-eluting particles, microparticles and nanoparticles). The stents may be intended for any vessel in the body, including neurological, carotid, vein graft, coronary, aortic, renal, iliac, femoral, popliteal vasculature, and urethral passages. An implantable device can be designed for the localized delivery of a therapeutic agent. A medicated implantable device may be constructed in part, e.g., by coating the device with a coating material containing a therapeutic agent. The body of the device may also contain a therapeutic agent.

An implantable device can be fabricated with a coating containing partially or completely a biodegradable/bioabsorbable/bioerodable polymer, a biostable polymer, or a combination thereof. An implantable device itself can also be fabricated partially or completely from a biodegradable/bioabsorbable/bioerodable polymer, a biostable polymer, or a combination thereof.

As used herein, a material that is described as a layer or a film (e.g., a coating) "disposed over" an indicated substrate (e.g., an implantable device) refers to, e.g., a coating of the material deposited directly or indirectly over at least a portion of the surface of the substrate. Direct depositing means that the coating is applied directly to the exposed surface of the substrate. Indirect depositing means that the coating is applied to an intervening layer that has been deposited directly or indirectly over the substrate. In some embodiments, the term a "layer" or a "film" excludes a film or a layer formed on a non-implantable device.

In the context of a stent, "delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

Decreasing Molecular Weight

The molecular weight of polymer forming the coating described herein can be reduced or decreased by various methods. The molecular weight can be decreased post coating of an implantable device prior to deployment of the implantable device (t=0) or after implantation of implantable device, e.g., by enhanced hydrolysis of the coating. Such methods include, e.g., one or a combination of the following:

1) prolonged e-beaming, multiple e-beaming post coating, e-beaming at a lower dose rate for a total longer time under the beam, or e-beaming at room temperature.

2) higher temperature treatment (e.g., treatment at 50° C. to 70° C.) of coated device (e.g., stent) for drying in a high humidity environment prior to vacuum/conventional drying. As used herein, the term "high humidity environment" refers to an environment having a degree of humidity higher than the ambient.

3) decreasing the BHT content in the coating.

4) addition of lactide monomers/oligomers in the coating.

5) addition of —COOH terminated oligomers of d,l PLA.

6) sterilization by gamma radiation at the same dose (i.e. 31 kGy) as would be used for e-beam.

6) addition of other plasticizers to the coating, e.g., ethyl lactate, DMSO, NMP, benzyl benzoate, which would lower the glass transition temperature ($T_g$) of the coating to accelerate degradation.

7) addition of a hygroscopic additive to the coating to increase water adsorption of D,L-PLA, if present, which hygroscopic additives can be, e.g., low MW PVP, low MW PEG. A higher water concentration in the coating increases hydrolysis rate, and the presence of water during irradiation sterilization will accelerate MW decrease in this step. Hygroscopic additive could be amphiphilic to allow better homogenicity.

8) addition of micronized $NaO_2$ or $KO_2$, or superoxide salts. These compounds are insoluble in organics but will cleave ester bonds quite actively when hydrated so as to decrease MW of the polymer in the coating.

9) addition of more stannous octoate to bring its level up to the maximum level allowed by the material specification. Stannous octate will increase MW drop during extrusion, e-beam sterilization, and in-vivo deployment.

10) addition of LMW D,L-PLA with a MW tuned to degrade within 3 to 6 months. Generally, such a LMW D,L-PLA would not form a coating of integrity. A primer formed of a HMW or VHMW resorbable polymer would make such a deficiency of the LMW D,L-PLA to allow forming a coating using such a LMW D,L-PLA. LMW D,L-PLA that degrades within 3 to 6 months generally have a molecular weight of below 60,000 Da.

11) forming micro-porous D,L-PLA coating by a process of controlled phase inversion kinetics. Such a micro-porous D,L-PLA coating allows for enhanced water uptake so as to increase hydrolysis of the coating. Phase inversion is within the general knowledge in the art since it is a commercially available process (used to fabricate membrane filters).

Biologically Active Agents

In some embodiments, the implantable device described herein can optionally include at least one biologically active ("bioactive") agent. The at least one bioactive agent can include any substance capable of exerting a therapeutic, prophylactic or diagnostic effect for a patient.

Examples of suitable bioactive agents include, but are not limited to, synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules that bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. The bioactive agents could be designed, e.g., to inhibit the activity of vascular smooth muscle cells. They could be directed at inhibiting abnormal or inappropriate migration and/or proliferation of smooth muscle cells to inhibit restenosis.

In certain embodiments, optionally in combination with one or more other embodiments described herein, the implantable device can include at least one biologically active agent selected from antiproliferative, antineoplastic, antimitotic, anti-inflammatory, antiplatelet, anticoagulant, antifibrin, antithrombin, antibiotic, antiallergic and antioxidant substances.

An antiproliferative agent can be a natural proteineous agent such as a cytotoxin or a synthetic molecule. Examples of antiproliferative substances include, but are not limited to, actinomycin D or derivatives and analogs thereof (manufactured by Sigma-Aldrich, or COSMEGEN available from Merck) (synonyms of actinomycin D include dactinomycin, actinomycin IV, actinomycin $I_1$, actinomycin $X_1$, and actinomycin $C_1$); all taxoids such as taxols, docetaxel, and paclitaxel and derivatives thereof; all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Examples of rapamycin derivatives include, but are not limited to, 40-O-(2-hydroxy)ethyl-rapamycin (trade name everolimus from Novartis), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus, manufactured by Abbott Labs.), ABT-578, novolimus, myolimus, deforolimus, temsirolimus, prodrugs thereof, co-drugs thereof, and combinations thereof. An anti-inflammatory drug can be a steroidal anti-inflammatory drug, a nonsteroidal anti-inflammatory drug (NSAID), or a combination thereof. Examples of anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol, clobetasol propionate, clobetasone butyrate, clopirac, cloticasone propionate, cormethasone acetate, cortodoxone, deflazacort, desonide, desoximetasone, dexamethasone, dexamethasone acetate, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

Alternatively, the anti-inflammatory agent can be a biological inhibitor of pro-inflammatory signaling molecules.

Anti-inflammatory biological agents include antibodies to such biological inflammatory signaling molecules.

In addition, the bioactive agents can be other than antiproliferative or anti-inflammatory agents. The bioactive agents can be any agent that is a therapeutic, prophylactic or diagnostic agent. In some embodiments, such agents can be used in combination with antiproliferative or anti-inflammatory agents. These bioactive agents can also have antiproliferative and/or anti-inflammatory properties or can have other properties such as antineoplastic, antimitotic, cystostatic, antiplatelet, anticoagulant, antifibrin, antithrombin, antibiotic, antiallergic, and/or antioxidant properties.

Examples of antineoplastics and/or antimitotics include, but are not limited to, paclitaxel (e.g., TAXOL® available from Bristol-Myers Squibb), docetaxel (e.g., Taxotere® from Aventis), methotrexate, azathioprine, vincristine, vinblastine, fluorouracil, doxorubicin hydrochloride (e.g., Adriamycin® from Pfizer), and mitomycin (e.g., Mutamycin® from Bristol-Myers Squibb).

Examples of antiplatelet, anticoagulant, antifibrin, and antithrombin agents that can also have cytostatic or antiproliferative properties include, but are not limited to, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as ANGIOMAX (from Biogen), calcium channel blockers (e.g., nifedipine), colchicine, fibroblast growth factor (FGF) antagonists, fish oil (e.g., omega 3-fatty acid), histamine antagonists, lovastatin (a cholesterol-lowering drug that inhibits HMG-CoA reductase, brand name Mevacor® from Merck), monoclonal antibodies (e.g., those specific for platelet-derived growth factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetics, 4-amino-2,2,6,6-tetramethylpiperidine-1-oxyl (4-amino-TEMPO), estradiol, anticancer agents, dietary supplements such as various vitamins, and a combination thereof.

Examples of cytostatic substances include, but are not limited to, angiopeptin, angiotensin converting enzyme inhibitors such as captopril (e.g., Capoten® and Capozide® from Bristol-Myers Squibb), cilazapril and lisinopril (e.g., Prinivil® and Prinzide® from Merck).

Examples of antiallergic agents include, but are not limited to, permirolast potassium. Examples of antioxidant substances include, but are not limited to, 4-amino-2,2,6,6-tetramethylpiperidine-1-oxyl (4-amino-TEMPO). Other bioactive agents include anti-infectives such as antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary vasodilators; peripheral and cerebral vasodilators; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents.

Other biologically active agents that can be used include alpha-interferon, genetically engineered epithelial cells, tacrolimus and dexamethasone.

A "prohealing" drug or agent, in the context of a blood-contacting implantable device, refers to a drug or agent that has the property that it promotes or enhances re-endothelialization of arterial lumen to promote healing of the vascular tissue. The portion(s) of an implantable device (e.g., a stent) containing a prohealing drug or agent can attract, bind and eventually become encapsulated by endothelial cells (e.g., endothelial progenitor cells). The attraction, binding, and encapsulation of the cells will reduce or prevent the formation of emboli or thrombi due to the loss of the mechanical properties that could occur if the stent was insufficiently encapsulated. The enhanced re-endothelialization can promote the endothelialization at a rate faster than the loss of mechanical properties of the stent.

The prohealing drug or agent can be dispersed in the body of the bioabsorbable polymer substrate or scaffolding. The prohealing drug or agent can also be dispersed within a bioabsorbable polymer coating over a surface of an implantable device (e.g., a stent).

"Endothelial progenitor cells" refer to primitive cells made in the bone marrow that can enter the bloodstream and go to areas of blood vessel injury to help repair the damage. Endothelial progenitor cells circulate in adult human peripheral blood and are mobilized from bone marrow by cytokines, growth factors, and ischemic conditions. Vascular injury is repaired by both angiogenesis and vasculogenesis mechanisms. Circulating endothelial progenitor cells contribute to repair of injured blood vessels mainly via a vasculogenesis mechanism.

In some embodiments, the prohealing drug or agent can be an endothelial cell (EDC)-binding agent. In certain embodiments, the EDC-binding agent can be a protein, peptide or antibody, which can be, e.g., one of collagen type 1, a 23 peptide fragment known as single chain Fv fragment (scFv A5), a junction membrane protein vascular endothelial (VE)-cadherin, and combinations thereof. Collagen type 1, when bound to osteopontin, has been shown to promote adhesion of endothelial cells and modulate their viability by the down regulation of apoptotic pathways. S. M. Martin, et al., *J. Biomed. Mater. Res.*, 70A:10-19 (2004). Endothelial cells can be selectively targeted (for the targeted delivery of immunoliposomes) using scFv A5. T. Volkel, et al., *Biochimica et Biophysica Acta*, 1663:158-166 (2004). Junction membrane protein vascular endothelial (VE)-cadherin has been shown to bind to endothelial cells and down regulate apoptosis of the endothelial cells. R. Spagnuolo, et al., *Blood*, 103:3005-3012 (2004).

In a particular embodiment, the EDC-binding agent can be the active fragment of osteopontin, (Asp-Val-Asp-Val-Pro-Asp-Gly-Asp-Ser-Leu-Ala-Try-Gly). Other EDC-binding agents include, but are not limited to, EPC (epithelial cell) antibodies, RGD peptide sequences, RGD mimetics, and combinations thereof.

In further embodiments, the prohealing drug or agent can be a substance or agent that attracts and binds endothelial progenitor cells. Representative substances or agents that attract and bind endothelial progenitor cells include antibodies such as CD-34, CD-133 and vegf type 2 receptor. An agent that attracts and binds endothelial progenitor cells can include a polymer having nitric oxide donor groups.

The foregoing biologically active agents are listed by way of example and are not meant to be limiting. Other biologically active agents that are currently available or that may be developed in the future are equally applicable.

In a more specific embodiment, optionally in combination with one or more other embodiments described herein, the implantable device of the invention comprises at least one biologically active agent selected from paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), ABT-578, novolimus, myolimus, temsirolimus, deforolimus, pimecrolimus, imatinib mesylate, midostaurin, clobetasol, progenitor cell-capturing antibodies, prohealing drugs, prodrugs thereof, co-drugs thereof, and a combination thereof. In a particular embodiment, the bioactive agent is everolimus. In another specific embodiment, the bioactive agent is dexamethasone acetate.

An alternative class of drugs would be p-para-α-agonists for increased lipid transportation, examples include fenofibrate.

In some embodiments, optionally in combination with one or more other embodiments described herein, the at least one biologically active agent specifically cannot be one or more of any of the bioactive drugs or agents described herein.

Coating Construct

According to some embodiments of the invention, optionally in combination with one or more other embodiments described herein, a coating disposed over an implantable device (e.g., a stent) can have a construct of any design. The coating can be a multi-layer structure that includes at least one primer layer described herein, which is layer (1) described below, and at least one reservoir layer, which is layer (2) described below, and can include any of the following (3), (4) and (5) layers or combination thereof:
(1) a primer layer;
(2) a reservoir layer (also referred to "matrix layer" or "drug matrix"), which can be a drug-polymer layer including at least one polymer (drug-polymer layer) or, alternatively, a polymer-free drug layer;
(3) a release control layer (also referred to as a "rate-limiting layer");
(4) a topcoat layer; and/or
(5) a finishing coat layer which is present to modulate the biological response the coating In some embodiments, a coating of the invention can include two or more reservoir layers described above, each of which can include a bioactive agent described herein.

Each layer of a coating can be disposed over the implantable device (e.g., a stent) by dissolving the invention polymer mixture or block copolymer, optionally with one or more other polymers, in a solvent, or a mixture of solvents, and disposing the resulting coating solution over the stent by spraying or immersing the stent in the solution. After the solution has been disposed over the stent, the coating is dried by allowing the solvent to evaporate. The process of drying can be accelerated if the drying is conducted at an elevated temperature. The complete stent coating can be optionally annealed at a temperature between about 40° C. and about 150° C. for a period of time between about 5 minutes and about 60 minutes, if desired, to allow for crystallization of the polymer coating, to finish physical aging of the polymer, and/or to improve the thermodynamic stability of the coating.

To incorporate a bioactive agent (e.g., a drug) into the reservoir layer, the drug can be combined with the polymer solution that is disposed over the implantable device as described above. Alternatively, if it is desirable a polymer-free reservoir can be made. To fabricate a polymer-free reservoir, the drug can be dissolved in a suitable solvent or mixture of solvents, and the resulting drug solution can be disposed over the implantable device (e.g., stent) by spraying or immersing the stent in the drug-containing solution.

Instead of introducing a drug via a solution, the drug can be introduced as a colloid system, such as a suspension in an appropriate solvent phase. To make the suspension, the drug can be dispersed in the solvent phase using conventional techniques used in colloid chemistry. Depending on a variety of factors, e.g., the nature of the drug, those having ordinary skill in the art can select the solvent to form the solvent phase of the suspension, as well as the quantity of the drug to be dispersed in the solvent phase. Optionally, a surfactant can be added to stabilize the suspension. The suspension can be mixed with a polymer solution and the mixture can be disposed over the stent as described above. Alternatively, the drug suspension can be disposed over the stent without being mixed with the polymer solution.

The drug-polymer layer can be applied indirectly over at least a portion of the stent surface to serve as a reservoir for at least one bioactive agent (e.g., drug) that is incorporated into the reservoir layer over at least a portion of the primer layer. The primer layer can be applied between the stent and the reservoir to improve the adhesion of the drug-polymer layer to the stent. The optional topcoat layer can be applied over at least a portion of the reservoir layer and serves as a rate-limiting membrane that helps to control the rate of release of the drug. In one embodiment, the topcoat layer can be essentially free from any bioactive agents or drugs. If the topcoat layer is used, the optional finishing coat layer can be applied over at least a portion of the topcoat layer for further control of the drug-release rate and for improving the biocompatibility of the coating. Without the topcoat layer, the finishing coat layer can be deposited directly on the reservoir layer.

Sterilization of a coated medical device generally involves a process for inactivation of micropathogens. Such processes are well known in the art. A few examples are e-beam, ETO sterilization, autoclaving, and gamma irradiation. Some of these processes can involve an elevated temperature or can be performed cold below room temperature. For example, ETO sterilization of a coated stent generally involves heating above 50° C. at humidity levels reaching up to 100% for periods of a few hours up to 24 hours. A typical ETO cycle would have the temperature in the enclosed chamber to reach as high as above 50° C. within the first 3-4 hours then and fluctuate between 40° C. to 50° C. for 17-18 hours while the humidity would reach the peak at 100% and maintain above 80% during the fluctuation time of the cycle.

If neither a finishing coat layer nor a topcoat layer is used, the stent coating could have only two layers—the primer and the reservoir.

Any layer of a coating, except for the primer layer, can contain any amount of bioresorbable, erodible or biodissolvable polymers. Non-limiting examples of such polymers include bioabsorbable polymers and biocompatible polymers include poly(N-vinyl pyrrolidone); polydioxanone; polyorthoesters; polyanhydrides; poly(glycolic acid); poly(glycolic acid-co-trimethylene carbonate); polyphosphoesters; polyphosphoester urethanes; poly(amino acids); poly(trimethylene carbonate); poly(iminocarbonates); co-poly(etheresters); polyalkylene oxalates; polyphosphazenes; biomolecules, e.g., fibrin, fibrinogen, cellulose, cellophane, starch, collagen, hyaluronic acid, and derivatives thereof (e.g., cellulose acetate, cellulose butyrate, cellulose acetate butyrate, cellulose nitrate, cellulose propionate, cellulose ethers, and carboxymethyl cellulose), polyurethane, polyesters, polycarbonates, polyurethanes, poly(L-lactic acid-co-caprolactone) (PLLA-CL), poly(D-lactic acid-co-caprolactone) (PDLA-CL), poly(DL-lactic acid-co-caprolactone) (PDLLA-CL), poly(D-lactic acid-glycolic acid (PDLA-GA), poly(L-lactic acid-glycolic acid (PLLA-GA), poly(DL-lactic acid-glycolic acid (PDLLA-GA), poly(L-lactic acid-co-caprolactone) (PLLA-CL), poly(D-lactic acid-co-caprolactone) (PDLA-CL), poly(DL-lactic acid-co-caprolactone) (PDLLA-CL), poly(glycolide-co-caprolactone) (PGA-CL), or any copolymers thereof.

Method of Fabricating Implantable Device

Other embodiments of the invention, optionally in combination with one or more other embodiments described herein, are drawn to a method of fabricating an implantable device. In one embodiment, the method comprises forming the implantable device of a material containing a biodegradable polymer or copolymer.

Under the method, a portion of the implantable device or the whole device itself can be formed of the material containing a biodegradable polymer or copolymer. The method can deposit a coating having a range of thickness over an implantable device. In certain embodiments, the method deposits over at least a portion of the implantable device a coating that has a thickness of ≤about 30 microns, or ≤about 20 microns, or ≤about 10 microns, or ≤about 5 microns.

In certain embodiments, the method is used to fabricate an implantable device selected from stents, grafts, stent-grafts, catheters, leads and electrodes, clips, shunts, closure devices, valves, and particles. In a specific embodiment, the method is used to fabricate a stent.

In some embodiments, to form an implantable device formed from a polymer, a polymer or copolymer optionally including at least one bioactive agent described herein can be formed into a polymer construct, such as a tube or sheet that can be rolled or bonded to form a construct such as a tube. An implantable device can then be fabricated from the construct. For example, a stent can be fabricated from a tube by laser machining a pattern into the tube. In another embodiment, a polymer construct can be formed from the polymeric material of the invention using an injection-molding apparatus. In yet another embodiment, a bioabsorbable implant can be fabricated by weaving fibers of bioabsorbable materials.

Non-limiting examples of polymers that can be used to fabricate an implantable device include poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(L-lactic acid-co-caprolactone) (PLLA-CL), poly(D-lactic acid-co-caprolactone) (PDLA-CL), poly(DL-lactic acid-co-caprolactone) (PDLLA-CL), poly(D-lactic acid-glycolic acid (PDLA-GA), poly(L-lactic acid-glycolic acid (PLLA-GA), poly(DL-lactic acid-glycolic acid (PDLLA-GA), poly(L-lactic acid-co-caprolactone) (PLLA-CL), poly(D-lactic acid-co-caprolactone) (PDLA-CL), poly(DL-lactic acid-co-caprolactone) (PDLLA-CL), poly(glycolide-co-caprolactone) (PGA-CL), poly(thioesters), poly(trimethylene carbonate), polyethylene amide, polyethylene acrylate, poly(glycolic acid-co-trimethylene carbonate), co-poly(ether-esters) (e.g., PEO/PLA), polyphosphazenes, biomolecules (e.g., fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (e.g., polyvinyl chloride), polyvinyl ethers (e.g., polyvinyl methyl ether), polyvinylidene halides (e.g., polyvinylidene chloride), poly(vinylidene fluoride), poly(vinylidene fluoride-co-hexafluoropropylene), polyacrylonitrile, polyvinyl ketones, polyvinyl aromatics (e.g., polystyrene), polyvinyl esters (e.g., polyvinyl acetate), acrylonitrile-styrene copolymers, ABS resins, polyamides (e.g., Nylon 66 and polycaprolactam), polycarbonates, polyoxymethylenes, polyimides, polyethers, polyurethanes, rayon, rayon-triacetate, cellulose and derivates thereof (e.g., cellulose acetate, cellulose butyrate, cellulose acetate butyrate, cellophane, cellulose nitrate, cellulose propionate, cellulose ethers, and carboxymethyl cellulose), and copolymers thereof.

Method of Treating or Preventing Disorders

An implantable device according to the present invention can be used to treat, prevent or diagnose various conditions or disorders. Examples of such conditions or disorders include, but are not limited to, atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, ureter obstruction and tumor obstruction. A portion of the implantable device or the whole device itself can be formed of the material, as described herein. For example, the material can be a coating disposed over at least a portion of the device.

In certain embodiments, optionally in combination with one or more other embodiments described herein, the inventive method treats, prevents or diagnoses a condition or disorder selected from atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, ureter obstruction and tumor obstruction. In a particular embodiment, the condition or disorder is atherosclerosis, thrombosis, restenosis or vulnerable plaque.

In one embodiment of the method, optionally in combination with one or more other embodiments described herein, the implantable device is formed of a material or includes a coating containing at least one biologically active agent selected from paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), ABT-578, novolimus, myolimus, temsirolimus, deforolimus, pimecrolimus, imatinib mesylate, midostaurin, clobetasol, progenitor cell-capturing antibodies, prohealing drugs, fenofibrate, prodrugs thereof, co-drugs thereof, and a combination thereof.

In certain embodiments, optionally in combination with one or more other embodiments described herein, the implantable device used in the method is selected from stents, grafts, stent-grafts, catheters, leads and electrodes, clips, shunts, closure devices, valves, and particles. In a specific embodiment, the implantable device is a stent.

While particular embodiments of the present invention have been shown and described, it will be obvious to those skilled in the art that changes and modifications can be made without departing from this invention in its broader aspects. Therefore, the claims are to encompass within their scope all such changes and modifications as fall within the true sprit and scope of this invention.

The invention claimed is:

1. A bioabsorbable coating on an implantable medical device, comprising a primer layer comprising a bioabsorbable polymer having a first molecular weight and a second layer comprising a bioabsorbable polymer of a second molecular weight and a drug, or a second layer comprising a bioabsorbable polymer of a second molecular weight that does not comprise a drug and is formed on top of a layer of drug on top of the primer layer,
wherein the first molecular weight is higher than the second molecular weight,
wherein either the primer layer or the second layer further comprises:
a plasticizer selected from the group consisting of ethyl lactate, DMSO, NMP, and benzyl benzoate, or
a hygroscopic additive selected from the group consisting of a low molecular weight PVP and a low molecular weight PEG, or
micronized $NaO_2$ or $KO_2$, or
stannous octoate, and
wherein the coating is completely or substantially completely absorbed upon implantation in a human body within a period from about 3 months to about 6 months.

2. The bioabsorbable coating of claim 1, wherein the bioabsorbable polymer having a first molecular weight in the primer layer is a high or very high molecular weight (HMW or VHMW) absorbable polymer.

3. The bioabsorbable coating of claim 1, wherein the bioabsorbable polymer having a second molecular weight in the second layer is a low molecular weight (LMW) absorbable polymer.

4. The bioabsorbable coating of claim 2, wherein the HMW or VHMW absorbable polymer is selected from PLLA, 85/15 PLGA, 75/25 PLGA, poly(ester amide), PLA-PCL-GA terpolymer, PCL-GA, and copolymers thereof.

5. The bioabsorbable coating of claim 3, wherein the LMW absorbable polymer is LMW D,L-PLA.

6. The bioabsorbable coating of claim 1, which is microporous and is formed by a process of controlled phase inversion kinetics, wherein the second layer and/or the primer layer comprises D,L-PLA.

7. The bioabsorbable coating of claim 1, wherein the implantable device is a stent.

8. The bioabsorbable coating of claim 1, wherein the drug is selected from the group consisting of paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), zotarolimus, novolimus, myolimus, temsirolimus, deforolimus, γ-hiridun, clobetasol, pimecrolimus, imatinib mesylate, midostaurin, fenofibrate, prodrugs thereof, co-drugs thereof, and combinations thereof.

9. A method of fabricating an implantable device that comprises a bioabsorbable coating, comprising:
forming a primer layer on the surface of an implantable device, the primer layer comprising a bioabsorbable polymer having a first molecular weight; and
forming a second layer comprising a bioabsorbable polymer having a second molecular weight and a drug, or forming a second layer comprising a bioabsorbable polymer having a second molecular weight that does not comprise a drug on a layer of drug on top of the primer layer, thereby forming the bioabsorbable coating, wherein the first molecular weight is higher than the second molecular weight,
wherein the bioabsorbable polymer having a first molecular weight in the primer layer is a high molecular weight (HMW) or very high molecular weight (VHMW) absorbable polymer,
wherein the bioabsorbable polymer having a second molecular weight in the second layer is a low molecular weight (LMW) absorbable polymer,
wherein either the primer layer or the second layer further comprises:
a plasticizer selected from the group consisting of ethyl lactate, DMSO, NMP, and benzyl benzoate, or
a hygroscopic additive selected from the group consisting of a low molecular weight PVP and a low molecular weight PEG, or
micronized $NaO_2$ or $KO_2$ or
stannous octoate, and
wherein the bioabsorbable coating is completely or substantially completely absorbed upon implantation in a human body within a period from about 3 months to about 6 months.

10. The method of claim 9, wherein the HMW or VHMW absorbable polymer is selected from PLLA, 85/15 PLGA, 75/25 PLGA, poly(ester amide), PLA-PCL-GA terpolymer, PCL-GA, and copolymers thereof.

11. The method of claim 9, wherein the LMW absorbable polymer is LMW D,L-PLA.

12. The method of claim 9, wherein the coating is microporous and is formed by a process of controlled phase inversion kinetics, wherein the second layer and/or the primer layer comprises D,L-PLA.

13. The method of claim 9, wherein the implantable device is a stent.

14. The method of claim 9, further comprising enhancing degradation rate of the coating.

15. The method of claim 14, wherein enhancing degradation rate comprises:
decreasing the molecular weight of the bioabsorbable polymer in the first and/or second post coating prior to deployment of the implantable device, or
enhancing rate of hydrolysis of the bioabsorbable polymer in the first and/or second layer.

16. The method of claim 14, wherein enhancing degradation rate of the coating comprises a step selected from:
i) prolonged e-beaming, multiple e-beaming post coating, e-beaming at a lower dose rate for a total longer time under the beam, or e-beaming at room temperature;
ii) higher temperature treatment of a coated implantable device drying in a high humidity environment prior to vacuum/conventional drying;
iii) decreasing BHT content in the coating if the coating comprises BHT;
iv) adding lactide monomers and/or oligomers in the coating;

v) adding —COOH terminated oligomers of D,L-PLA in the coating;
vi) sterilization by gamma radiation at same dose as is used for e-beam sterilization;
vii) adding LMW D,L-PLA with a MW tuned to degrade within 3 to 6 months;
viii) forming micro-porous D,L-PLA coating by a process of controlled phase inversion; and
ix) any combination of step i)-viii).

17. A method of treating a vascular medical condition, comprising implanting in a patient an implantable medical device comprising the bioabsorbable coating according to claim 1, wherein the implantable medical device is a stent; wherein the vascular medical condition is selected from restenosis, atherosclerosis, thrombosis, or combinations thereof.

18. The method of claim 9, wherein the drug is selected from the group consisting of paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), zotarolimus, novolimus, myolimus, temsirolimus, deforolimus, γ-hiridun, clobetasol, pimecrolimus, imatinib mesylate, midostaurin, fenofibrate, prodrugs thereof, co-drugs thereof, and combinations thereof.

* * * * *